United States Patent [19]
Zagar et al.

[11] Patent Number: 5,962,694
[45] Date of Patent: Oct. 5, 1999

[54] SUBSTITUTED 1-METHYL-3-PHENYLPYRAZOLES AND THE USE THEREOF AS HERBICIDES AND FOR THE DESICCATION OR DEFOLIATION OF PLANTS

[75] Inventors: Cyrill Zagar; Albrecht Harreus, both of Ludwigshafen; Christoph-Sweder von dem Bussche-Hünnefeld, Mannheim; Gerhard Hamprecht, Weinheim; Elisabeth Heistracher, Mannheim; Peter Schäfer, Ottersheim; Olaf Menke, Altleiningen; Karl-Otto Westphalen, Speyer; Ulf Misslitz, Neustadt; Helmut Walter, Obrigheim, all of Germany

[73] Assignee: BASF Aktiengesellschaft, Ludwigshafen, Germany

[21] Appl. No.: 09/068,306

[22] PCT Filed: Nov. 5, 1996

[86] PCT No.: PCT/EP96/04819

§ 371 Date: May 7, 1998

§ 102(e) Date: May 7, 1998

[87] PCT Pub. No.: WO97/18195

PCT Pub. Date: May 22, 1997

[30] Foreign Application Priority Data

Nov. 15, 1995 [DE] Germany ............... 195 42 520

[51] Int. Cl.⁶ .................. A01N 43/56; C07D 231/20
[52] U.S. Cl. .............. 548/366.1; 504/169; 504/282
[58] Field of Search .............. 548/366.1; 504/282, 504/169

[56] References Cited

U.S. PATENT DOCUMENTS

| | | | |
|---|---|---|---|
| 4,298,749 | 11/1981 | Plath et al. | 548/377 |
| 4,316,040 | 2/1982 | Plath et al. | 548/377 |
| 5,077,142 | 12/1991 | Sakon et al. | 428/690 |

FOREIGN PATENT DOCUMENTS

| | | |
|---|---|---|
| 516982 | 12/1992 | European Pat. Off. . |
| 530832 | 3/1993 | European Pat. Off. . |
| 3163063 | 8/1988 | Japan . |
| 3151367 | 11/1989 | Japan . |
| 6199805 | 9/1992 | Japan . |
| 92/02509 | 2/1992 | WIPO . |
| 95/24403 | 9/1995 | WIPO . |
| 95/34659 | 12/1995 | WIPO . |
| 96/01255 | 1/1996 | WIPO . |
| 96/15115 | 5/1996 | WIPO . |
| 97/00246 | 1/1997 | WIPO . |

OTHER PUBLICATIONS

Chem. Abst., vol. 115, No. 5, Aug. 5, 1991.

*Primary Examiner*—Robert W. Ramsuer
*Attorney, Agent, or Firm*—Keil & Weinkauf

[57] ABSTRACT

Substituted 1-methyl-3-phenylpyrazoles I and their agriculturally useful acid addition salts

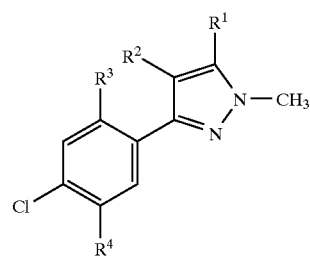

where $R^1 = C_1-C_4$-haloalkoxy or $C_1-C_4$-haloalkylthio;

$R^2 =$ halogen; $R^3 =$ F or Cl;

$R^4 =$ CN, $C_1-C_4$-fluoroalkyl, $C_2-C_4$-fluoroalkenyl or $-C(R^5)(X-R^6)(Y-R^7)$;

$R^5 =$ H or $C_1-C_4$-alkyl; X and Y=—O— or —S—;

$R^6$, $R^7 = C_1-C_4$-alkyl, $C_1-C_4$-haloalkyl, $C_3-C_4$-alkenyl, $C_3-C_4$-haloalkenyl or $C_3-C_4$-alkynyl;

are used as herbicides; for the desiccation/defoliation of plants.

11 Claims, No Drawings

SUBSTITUTED 1-METHYL-3-PHENYLPYRAZOLES AND THE USE THEREOF AS HERBICIDES AND FOR THE DESICCATION OR DEFOLIATION OF PLANTS

The present invention relates to new substituted 1-methyl-3-phenylpyrazoles of the formula I

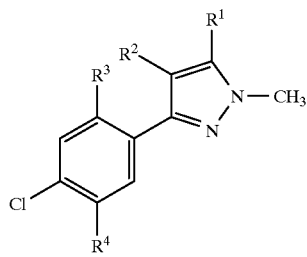

where the substituents have the following meanings:

$R^1$ is $C_1$–$C_4$-haloalkoxy or $C_1$–$C_4$-haloalkylthio;

$R^2$ is halogen;

$R^3$ is fluorine or chlorine;

$R^4$ is cyano, $C_1$–$C_4$-fluoroalkyl, $C_2$–$C_4$-fluoroalkenyl or —C($R^5$)(X-$R^6$)(Y-$R^7$), where $R^5$ is hydrogen or $C_1$–$C_4$-alkyl, X and Y independently of one another are oxygen or sulfur and $R^6$ and $R^7$ independently of one another are $C_1$–$C_4$-alkyl, $C_1$–$C_4$-haloalkyl, $C_3$–$C_4$-alkenyl, $C_3$–$C_4$-haloalkenyl or $C_3$–$C_4$-alkynyl;

and to the agriculturally useful acid addition salts of I.

Furthermore, the invention relates to the use of the compounds I as herbicides or for the desiccation/defoliation of plants, herbicidal compositions and compositions for the desiccation/defoliation of plants which comprise the compounds I as active ingredients, processes for the preparation of herbicidal compositions and compositions for the desiccation/defoliation of plants using the compounds I, and methods for controlling undesirable vegetation and for the desiccation/defoliation of plants using the compounds I.

In WO 95/24403, many heterocycles having the common radical —S(O)$_{0-2}$—CH$_2$CH$_2$CH=CF$_2$— inter alia 4-cyano-5-(4,4-difluorobut-3-enylthio)-1-methyl-3-phenylpyrazole—are reported as having nematicidal, insecticidal and acaricidal properties.

Furthermore, JP-A 03/072 460 describes herbicidally active phenylpyrazole derivatives of the formula II

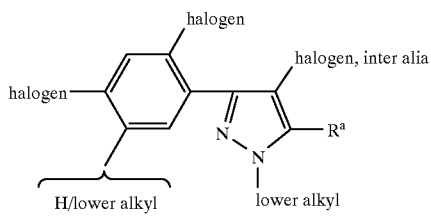

where $R^a$ can be, inter alia, halogen-substituted lower alkoxy or lower alkylthio.

Furthermore, JP-A 03/151 367 discloses, as herbicides, 1-lower-alkyl-3-(2,4-dihalophenyl)-4-halo-5-(haloalkoxy)pyrazoles which have attached to them in the 5-position on the phenyl ring a 1,3-dioxolan-2-yl group, inter alia.

JP 06/199 805 discloses a process for the preparation of herbicidally active 1-H- and 1-lower-alkyl-3-(dihalophenyl)-4-halogen-5-(haloalkoxy/haloalkylthio)pyrazoles which can have attached to them in the 5-position on the phenyl ring halogen or lower alkoxy, inter alia. Moreover, there can be found in JP-A 03/163 063 herbicidally active phenylpyrazoles of the general formula III

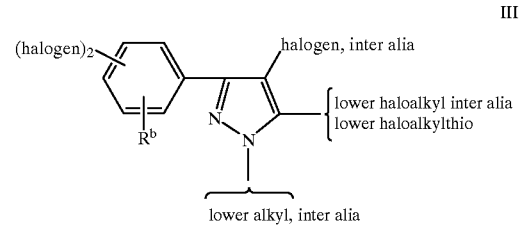

where $R^b$ can be, inter alia, formyl, alkoxy, alkylthio, haloalkoxy, haloalkylthio, lower alkenyloxy, lower alkenylthio, lower haloalkenyloxy, lower haloalkenylthio, lower alkynyloxy or lower alkynylthio.

WO 92/02509 relates to pyrazole derivatives which are substituted by phenyl and alkylsulfonyl and which are also reported as having a herbicidal action. Substances which are suitable for their preparation are, inter alia, compounds of type I.

Other herbicides of the type of the compounds I can also be seen in the earlier WO 95/34659.

Finally, some of the substituted 1-methyl-3-phenylpyrazoles I formally come under the general formulae of the 3-phenylpyrazoles in the earlier Patent Applications WO 96/01255 and WO 96/15115.

However, the herbicidal properties of the prior art phenylpyrazoles with a view to the harmful plants are not always entirely satisfactory. It was therefore the object of the present invention to provide novel herbicidally active 3-phenylpyrazoles which allow better control of undesirable plants. Another object was to provide novel compounds which have a desiccant or defoliant action.

We have found that this object is achieved by the present substituted 1-methyl-3-phenylpyrazoles of the formula I and their herbicidal action. We have furthermore found herbicidal compositions which comprise the compounds I and have a very good herbicidal activity. Moreover, we have found processes for the preparation of these compositions and methods for controlling undesirable vegetation using the compounds I.

We have furthermore found that the compounds I are also suitable for the desiccation/defoliation of parts of plants, suitable plants being crop plants such as cotton, potatoes, oilseed rape, sunflower, soybean or field beans, in particular cotton. Thus, we have found compositions for the desiccation and/or defoliation of plants, processes for the preparation of these compositions and methods for the desiccation and/or defoliation of plants using the compounds I.

Depending on the substitution pattern, the compounds of the formula I can contain one or more chiral centers, in which case they exist in the form of enantiomer or diastereomer mixtures. The invention relates to the pure enantiomers or diastereomers and also to their mixtures.

Agriculturally useful acid addition salts of I are generally to be understood as meaning the salts of I with acids whose anions do not adversely affect the herbicidal action of the compounds I. Accordingly, anions which are mainly suitable are fluoride, chloride, bromide, hydrogen sulfate, sulfate, dihydrogen phosphate, hydrogen phosphate, phosphate, nitrate, hydrogen carbonate, carbonate, hexafluorosilicate, hexafluorophosphate, benzoate, oxalate, dodecylbenzenesulfonate, and the anions of $C_1$–$C_4$-alkanoic acids, preferably formate, acetate, propionate and butyrate.

The organic moieties mentioned for the substituents $R^1$ and $R^4$ to $R^7$ are collective terms for individual enumerations of the individual group members. All carbon chains, i.e. all alkyl, fluoroalkyl, haloalkyl, haloalkoxy, haloalkylthio, alkenyl, fluoroalkenyl, haloalkenyl and alkynyl moieties, can be straight-chain or branched. Halogenated substituents preferably have attached to them one to five identical or different halogen atoms. The meaning of halogen represents in each case fluorine, bromine, chlorine or iodine, in particular fluorine or chlorine.

Other examples of meanings are, for example:

- $C_1$–$C_4$-alkyl: methyl, ethyl, n-propyl, 1-methylethyl, n-butyl, 1-methylpropyl, 2-methylpropyl or 1,1-dimethylethyl, in particular methyl or ethyl;
- $C_1$–$C_4$-fluoroalkyl: a $C_1$–$C_4$-alkyl radical as mentioned above which is partially or fully substituted by fluorine, eg. $CHF_2$, $CH_2F$, $CF_3$, 2-fluoroethyl, 1,1-difluoroethyl, 2,2,2-trifluoroethyl, 1,1,2,2-tetrafluoroethyl, $C_2F_5$, 3-fluoropropyl, 1,1-difluoropropyl, 3,3,3-trifluoropropyl, heptafluoropropyl, heptafluoro-1-methylethyl, 4-fluorobutyl, 1,1-difluorobutyl, 4,4,4-trifluorobutyl or nonafluorobutyl, in particular $CH_2F$, $CHF_2$, $CF_3$, $C_2F_5$ or heptafluoropropyl;
- $C_1$–$C_4$-haloalkyl: a $C_1$–$C_4$-alkyl radical as mentioned above which is partially or fully substituted by fluorine, chlorine, bromine and/or iodine, eg. 2-fluoroethyl, 2,2,2-trifluoroethyl, 2-chloroethyl, 2,2-dichloroethyl, 2,2,2-trichloroethyl, 2-bromoethyl, 2-iodoethyl, 3-fluoropropyl, 2,3-difluoropropyl, 3,3,3-trifluoropropyl, 2,2,3,3-tetrafluoropropyl, 2,3-dichloro-2,3-difluoropropyl, 3-chloropropyl, 2,3-dichloropropyl, 3,3,3-trichloropropyl, 2,2,3,3-tetrachloropropyl, 3-bromopropyl, 2,3-dibromopropyl, 3-iodopropyl, 4-fluorobutyl, 2,3-difluorobutyl, 3,4-difluorobutyl, 4,4,4-trifluorobutyl, 4-chlorobutyl, 2,3-dichlorobutyl, 3,4-dichlorobutyl, 4,4,4-trichlorobutyl, 4-bromobutyl or 4-iodobutyl, in particular 2-fluoroethyl, 2,2,2-trifluoroethyl, 2-chloroethyl, 3-chloropropyl or 4-chlorobutyl;
- $C_1$–$C_4$-haloalkoxy: $C_1$–$C_4$-alkoxy, such as $OCH_3$, $OC_2H_5$, $OCH_2$—$C_2H_5$, $OCH(CH_3)_2$, n-butoxy, 1-methylpropoxy, 2-methylpropoxy or $OC(CH_3)_3$, in particular $OCH_3$, which is partially or fully substituted by fluorine, chlorine, bromine and/or iodine, eg. $OCH_2Cl$, $OCH_2F$, $OCHF_2$, $OCF_3$, chlorodifluoromethoxy, 2-fluoroethoxy, 2-bromoethoxy, 2-iodoethoxy, 2,2-difluoroethoxy, 2,2,2-trifluoroethoxy, 2,2,2-trichloroethoxy, $OC_2F_5$, 3-fluoropropoxy, 3-chloropropoxy, 3-bromopropoxy, 3-iodopropoxy, 2,3-difluoropropoxy, 3,3,3-trifluoropropoxy, 2,2,3,3-tetrafluoropropoxy, heptafluoropropoxy, heptafluoro-1-methylethoxy, 4-fluorobutoxy or 4-chlorobutoxy, preferably difluoromethoxy, chlorodifluoromethoxy or $OCF_3$;
- $C_1$–$C_4$-haloalkylthio: $C_1$–$C_4$-alkylthio, such as $SCH_3$, $SC_2H_5$, $SCH_2$—$C_2H_5$, $SCH(CH_3)_2$, n-butylthio, 1-methylpropylthio, 2-methylpropylthio or $SC(CH_3)_3$, in particular $SCH_3$, which is partially or fully substituted by fluorine, chlorine, bromine and/or iodine, eg. $SCH_2Cl$, $SCH_2F$, $SCHF_2$, $SCF_3$, chlorodifluoromethylthio, 2-fluoroethylthio, 2-bromoethylthio, 2-iodoethylthio, 2,2-difluoroethylthio, 2,2,2-trifluoroethylthio, 2,2,2-trichloroethylthio, $SC_2F_5$, 3-fluoropropylthio, 3-chloropropylthio, 3-bromopropylthio, 3-iodopropylthio, 2,3-difluoropropylthio, 3,3,3-trifluoropropylthio, 2,2,3,3-tetra-fluoropropylthio, heptafluoropropylthio, heptafluoro-1-methylethylthio, 4-fluorobutylthio or 4-chlorobutylthio, preferably difluoromethylthio, chlorodifluoromethylthio or $SCF_3$;
- $C_2$–$C_4$-fluoroalkenyl: $C_2$–$C_4$-alkenyl, such as ethenyl, prop-1-en-1-yl, prop-2-en-1-yl, 1-methylethenyl, but-1-en-1-yl, but-2-en-1-yl, but-3-en-1-yl, but-1-en-2-yl, but-3-en-2-yl, 2-methylprop-2-en-1-yl or 2-methylprop-1-en-1-yl, which is partially or fully substituted by fluorine, eg. 1-fluoroethenyl, 2-fluoroethenyl, 2,2-difluoroethenyl, 1,2-difluoroethenyl, trifluoroethenyl, 1-fluoroprop-1-en-1-yl, pentafluoroprop-1-en-1-yl, 3,3-difluoroprop-2-en-1-yl, pentafluoroprop-2-en-1-yl, pentafluoro-1-methylethenyl, 1-fluorobut-1-en-1-yl, 4,4,4-trifluorobut-1-en-1-yl, heptafluorobut-1-en-1-yl, 4,4-difluorobut-3-en-1-yl or 3,3,3-trifluoro-2-methylprop-1-en-1-yl, preferably 1-fluoroethenyl, trifluoroethenyl or pentafluoroprop-1-en-1-yl;
- $C_3$–$C_4$-alkenyl: prop-2-en-1-yl, but-2-en-1-yl, but-3-en-1-yl, but-3-en-2-yl or 2-methylprop-2-en-1-yl;
- $C_3$–$C_4$-haloalkenyl: $C_3$–$C_4$-alkenyl as mentioned above which is partially or fully substituted by fluorine, chlorine, bromine and/or iodine, eg. 2-chloroprop-2-en-1-yl, 3-chloroprop-2-en-1-yl, 3,3-dichloroprop-2-en-1-yl, 3-bromoprop-2-en-1-yl, 3-fluoroprop-2-en-1-yl, 4,4-difluorobut-3-en-1-yl or 4,4-dichlorobut-3-en-1-yl;
- $C_3$–$C_4$-alkynyl: prop-2-yn-1-yl, but-2-yn-1-yl, but-3-yn-1-yl or but-3-yn-2-yl.

Preferred with a view to the use of the substituted 1-methyl-3-phenylpyrazoles I as herbicides are those compounds I where the substituents have the following meanings, in each case alone or in combination:

$R^1$ is difluoromethoxy, chlorodifluoromethoxy, $OCF_3$ or difluoromethylthio, in particular difluoromethoxy;

$R^2$ is chlorine or bromine, in particular chlorine;

$R^3$ is fluorine;

$R^4$ is cyano, fluoromethyl, difluoromethyl, trifluoromethyl, pentafluoroethyl, heptafluoropropyl, 1-fluoroethenyl, 2,2-difluoroethenyl, trifluoroethenyl, pentafluoroprop-1-en-1-yl or —$C(R^5)(X-R^6)(Y-R^7)$, in particular fluoromethyl, difluoromethyl, trifluoromethyl or —$C(R^5(X-R^6(Y-R^7)$;

$R^5$ is hydrogen, methyl or ethyl, in particular hydrogen;

X and Y are both oxygen or both sulfur;

$R^6$ and $R^7$ independently of one another are $C_1$–$C_4$-alkyl, $C_1$–$C_4$-haloalkyl or $C_3$–$C_4$-alkenyl, in particular methyl, ethyl, n-propyl or allyl.

Very especially preferred are the compounds Ia (= I where $R^1$=difluoromethoxy; $R^2$ and $R^3$=chlorine) which are listed in Table 1 below:

TABLE 1

Ia

| No. | —$R^4$ |
|---|---|
| Ia.001 | —CH(OCH$_3$)$_2$ |
| Ia.002 | —CH(OC$_2$H$_5$)$_2$ |
| Ia.003 | —CH(OCH$_2$—CH$_2$F)$_2$ |
| Ia.004 | —CH(OCH$_2$—CH$_2$Cl)$_2$ |
| Ia.005 | —CH(OC$_3$H$_7$)$_2$ |
| Ia.006 | —CH(OC$_4$H$_9$)$_2$ |
| Ia.007 | —CH(OCH$_2$—CH(CH$_3$)$_2$)$_2$ |
| Ia.008 | —CH(OCH$_2$—CH=CH$_2$)$_2$ |
| Ia.009 | —CH(OCH$_2$—CH=CHCl)$_2$ |
| Ia.010 | —CH(OCH$_2$—C≡CH)$_2$ |
| Ia.011 | —CH(SCH$_3$)$_2$ |
| Ia.012 | —CH(SC$_2$H$_5$)$_2$ |
| Ia.013 | —CH(SCH$_2$—CH$_2$F)$_2$ |
| Ia.014 | —CH(SCH$_2$—CH$_2$Cl)$_2$ |
| Ia.015 | —CH(SC$_3$H$_7$)$_2$ |
| Ia.016 | —CH(SC$_4$H$_9$)$_2$ |
| Ia.017 | —CH(SCH$_2$—CH(CH$_3$)$_2$)$_2$ |
| Ia.018 | —CH(SCH$_2$—CH=CH$_2$)$_2$ |
| Ia.019 | —CH(SCH$_2$—CH=CHCl)$_2$ |
| Ia.020 | —CH(SCH$_2$—C≡CH)$_2$ |
| Ia.021 | —CH(OCH$_3$) (SCH$_3$) |
| Ia.022 | —CH(OCH$_3$) (SC$_2$H$_5$) |
| Ia.023 | —CH(OC$_2$H$_5$) (SCH$_3$) |
| Ia.024 | —CH(OC$_2$H$_5$) (SC$_2$H$_5$) |
| Ia.025 | —C(CH$_3$) (OCH$_3$)$_2$ |
| Ia.026 | —C(CH$_3$) (OC$_2$H$_5$)$_2$ |
| Ia.027 | —C(CH$_3$) (OCH$_2$—CH$_2$F)$_2$ |
| Ia.028 | —C(CH$_3$) (OCH$_2$—CH$_2$Cl)$_2$ |
| Ia.029 | —C(CH$_3$) (OC$_3$H$_7$)$_2$ |
| Ia.030 | —C(CH$_3$) (OC$_4$H$_9$) |
| Ia.031 | —C(CH$_3$) (OCH$_2$—CH(CH$_3$)$_2$)$_2$ |
| Ia.032 | —C(CH$_3$) (OCH$_2$—CH=CH$_2$)$_2$ |
| Ia.033 | —C(CH$_3$) (OCH$_2$—CH=CHCl)$_2$ |
| Ia.034 | —C(CH$_3$) (OCH$_2$—C≡CH)$_2$ |
| Ia.035 | —C(CH$_3$) (SCH$_3$)$_2$ |
| Ia.036 | —C(CH$_3$) (SC$_2$H$_5$)$_2$ |
| Ia.037 | —C(CH$_3$) (SCH$_2$—CH$_2$F)$_2$ |
| Ia.038 | —C(CH$_3$) (SCH$_2$—CH$_2$Cl)$_2$ |
| Ia.039 | —C(CH$_3$) (SC$_3$H$_7$)$_2$ |
| Ia.040 | —C(CH$_3$) (SC$_4$H$_9$)$_2$ |
| Ia.041 | —C(CH$_3$) (SCH$_2$—CH(CH$_3$)$_2$)$_2$ |
| Ia.042 | —C(CH$_3$) (SCH$_2$—CH=CH$_2$)$_2$ |
| Ia.043 | —C(CH$_3$) (SCH$_2$—CH=CHCl)$_2$ |
| Ia.044 | —C(CH$_3$) (SCH$_2$—C≡CH)$_2$ |
| Ia.045 | —C(CH$_3$) (OCH$_3$) (SCH$_3$) |
| Ia.046 | —C(CH$_3$) (OCH$_3$) (SC$_2$H$_5$) |
| Ia.047 | —C(CH$_3$) (OC$_2$H$_5$) (SCH$_3$) |
| Ia.048 | —C(CH$_3$) (OC$_2$H$_5$) (SC$_2$H$_5$) |
| Ia.049 | —CN |
| Ia.050 | —CH$_2$F |
| Ia.051 | —CHF$_2$ |
| Ia.052 | —CF$_3$ |
| Ia.053 | —CF$_2$—CH$_3$ |
| Ia.054 | —CH$_2$—CF$_3$ |

TABLE 1-continued

Ia

| No. | —$R^4$ |
|---|---|
| Ia.055 | —CH$_2$—CH$_2$F |
| Ia.056 | —CHF—CH$_2$F |
| Ia.057 | —CF$_2$—CF$_3$ |
| Ia.058 | —CF$_2$—CHF$_2$ |
| Ia.059 | —CH$_2$—CH$_2$—CH$_2$F |
| Ia.060 | —CH$_2$—CHF—CH$_2$F |
| Ia.061 | —CH$_2$—CH$_2$—CF$_3$ |
| Ia.062 | —CF$_2$—CH$_2$—CH$_3$ |
| Ia.063 | —CF$_2$—CF$_2$—CF$_3$ |
| Ia.064 | —CF(CF$_3$)$_2$ |
| Ia.065 | —CH$_2$—CH$_2$—CH$_2$—CH$_2$F |
| Ia.066 | —CF$_2$—CH$_2$—CH$_2$—CH$_3$ |
| Ia.067 | —CH$_2$—CH$_2$—CH$_2$—CF$_3$ |
| Ia.068 | —CF$_2$—CF$_2$—CF$_2$—CF$_3$ |
| Ia.069 | —CF=CH$_2$ |
| Ia.070 | —CH=CHF |
| Ia.071 | —CH=CF$_2$ |
| Ia.072 | —CF=CHF |
| Ia.073 | —CF=CF$_2$ |
| Ia.074 | —CF=CH$_2$—CH$_3$ |
| Ia.075 | —CF=CF$_2$—CF$_3$ |

Other especially preferred 3-phenylpyrazoles of the formulae Ib to Id are in particular the compounds Ib.001–Ib.075, which differ from the corresponding compounds Ia.001–Ia.075 only by the fact that $R^3$ is fluorine:

Ib the compounds Ic.001–Ic.075, which differ from the corresponding compounds Ia.001–Ia.075 only by the fact that $R^2$ is bromine:

Ic the compounds Id.001–Id.075, which differ from the corresponding compounds Ia.001–Ia.075 only by the fact that $R^2$ is bromine and $R^3$ is fluorine:

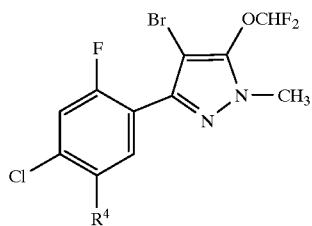

Id

The substituted 1-methyl-3-phenylpyrazoles of the formula I can be obtained in a variety of ways, in particular following one of the processes below:

A) Reaction of a β-ketocarboxylic acid derivative IV with methylhydrazine in an inert solvent (cf., for example, JP-A 04/225 937 and JP-A 03/072 460) and alkylation of the process product V:

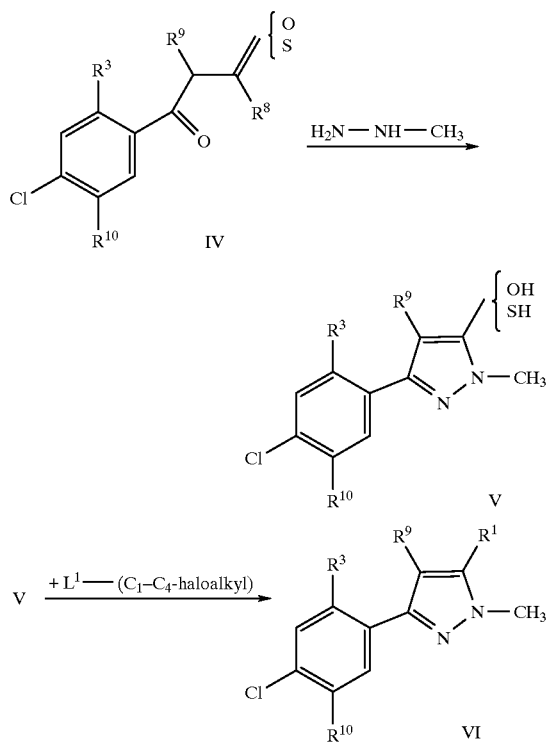

$L^1$ is a customary leaving group, such as halogen, —O—SO$_2$CH$_3$, —O—SO$_2$CF$_3$, —O—SO$_2$C$_4$F$_9$ and —O—SO$_2$(p-CH$_3$—C$_6$H$_4$);

$R^8$ is preferably halogen, $C_1$–$C_4$-alkoxy or ($C_1$–$C_4$-alkyl)-carbonyloxy;

$R^9$ is hydrogen or halogen;

$R^{10}$ is methyl, bromine or iodine.

The solvent can be aprotic or protic. Suitable examples are organic acids such as acetic acid, hydrocarbons, halogenated hydrocarbons, ethers such as ethylene glycol dimethyl ether, alcohols such as methanol and ethanol, and sulfoxides. However, the process may also be carried out in the absence of a solvent.

The reaction temperature is mainly determined by the melting point of the solvent or the compound IV and the boiling point of the reaction mixture. The process is preferably carried out at from approximately 60 to 120° C.

In general, approximately 0.95 to 5 times the molar amount, preferably 1 to 1.4 times the amount, of methylhydrazine is employed based on the β-ketocarboxylic acid derivative IV.

The amount of alkylating agent $L^1$-($C_1$–$C_4$-haloalkyl) is usually also 0.95 up to 5 times the molar amount based on the intermediate V.

The alkylation is normally carried out with the halide, preferably the chloride or bromide, or with the sulfate of an alkane or haloalkane, if desired in the presence of an organic base, eg. a trialkylamine, or of pyridine, or of an inorganic base, eg. of an alkali metal carbonate.

The alkylation is expediently carried out in an inert organic solvent, eg. in an aliphatic or cyclic ether such as 1,2-dimethoxyethane, tetrahydrofuran and dioxane, in an aliphatic ketone such as acetone, in an amide such as dimethylformamide, in a sulfoxide such as dimethyl sulfoxide or in a mixture of one of these solvents and water.

The reaction can generally be carried out at from 0° C. to the boiling point of the reaction mixture. It is preferably carried out at from approximately 20 to 80° C.

B) Halogenation of the compounds VI where $R^9$=hydrogen:

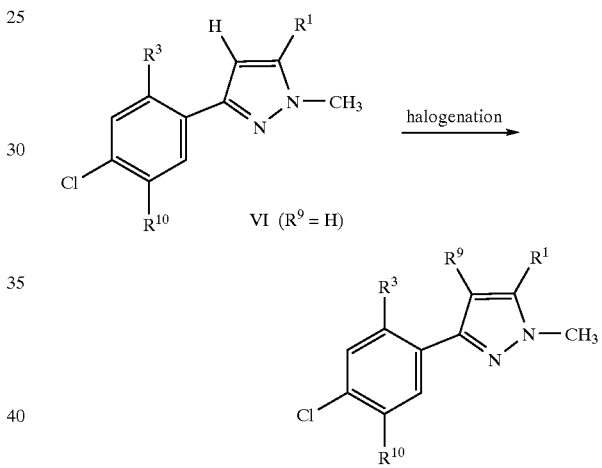

The reaction can be carried out in an inert solvent/diluent or in the absence of a solvent.

Examples of suitable solvents are organic acids, inorganic acids, hydrocarbons, halogenated hydrocarbons, aromatic hydrocarbons, ethers, sulfides, sulfoxides and sulfones.

Examples of suitable halogenating agents are chlorine, bromine, N-bromosuccinimides, N-chlorosuccinimides or sulfuryl chloride. Depending on the starting compound and the halogenating agent, the addition of a free-radical initiator, for example an organic peroxide such as dibenzoyl peroxide or an azo compound such as azobisisobutyronitrile, or irradiation with light, may have an advantageous effect on the course of the reaction.

The amount of halogenating agent is not critical. Both sub-stoichiometric amounts and large excesses of halogenating agent based on the compound VI to be halogenated (where $R^9$=hydrogen) are possible.

When using a free-radical initiator, a catalytic amount is usually sufficient.

The reaction temperature is normally at from (−100) to 200° C., mainly at from 10 to 100° C. or the boiling point of the reaction mixture.

C) Halogenation of compounds VII where $R^{10}$=methyl and, if desired, conversion of the process products VIII into compounds I:

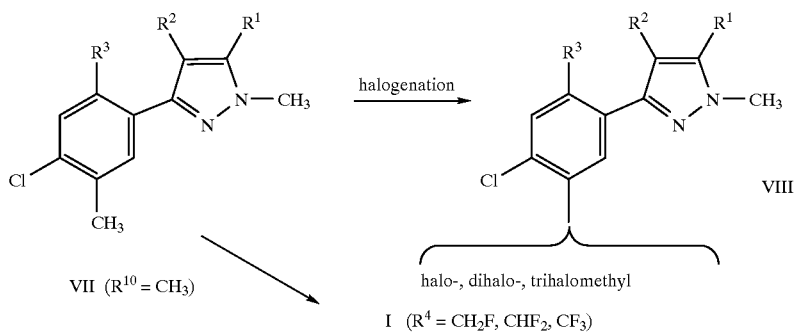

The halogenation of VII where $R^{10}=CH_3$ is preferably a chlorination or bromination. As regards suitable solvents, reaction conditions and ratios, reference is made to the information given under B). For example, the fluorination of VII ($R^{10}=CH_3$) to compounds I where $R^4=CH_2F$, $CHF_2$ or $CF_3$ can be carried out in a manner known per se by reaction with hydrogen fluoride and chlorine (see, for example, U.S. Pat. No. 4,825,014).

Those halogenation process products which have attached to them chloro-, bromo-, dichloro-, dibromo-, trichloro- or tribromomethyl instead of $R^4$ can be converted into compounds I where $R^4=CH_2F$, $CHF_2$ or $CF_3$ by means of nucleophilic substitution with fluoride (see, for example, AU 526 817 or P. L. Coe, D. Oldfield, J. C. Tatlow, J. Fluorine Chem. 29 (1985) 341). Examples of fluorides suitable for this purpose are alkali metal fluorides, which are employed in stoichiometric amounts or in an excess (up to approximately five times the molar amount based on the compound to be fluorinated):

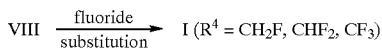

The fluorination is preferably carried out in a polar organic solvent such as dimethylformamide and sulfolane. A reaction temperature of from 50 to 300° C. is usually sufficient.

Process products VIII which have attached to them a dihalomethyl, preferably a dichloro- or dibromomethyl, group instead of $R^4$ can furthermore be reacted with alcohols or thiols (preferably thiols) $R^6$-XH in the presence of a strong base, such as sodium hydride, or with a salt $R^6$-XM, M being, in particular, an alkali metal, to give (thio)acetals I $\{R^4=\!\!-\!\!CH(X-R^6)_2\}$:

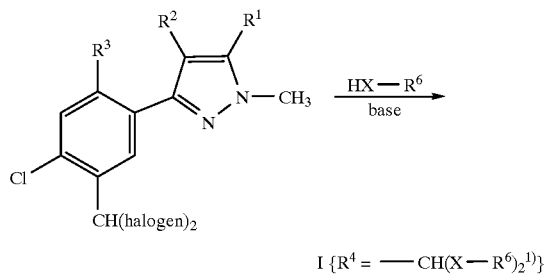

[1]) In this case, X=Y and $R^6=R^7$.

As regards suitable solvents, ratios and reaction conditions, the information given in the previous section preferably applies.

Compounds VIII which have a dihalomethyl or trihalomethyl radical can furthermore be converted into aldehydes or carboxylic acids IX by means of acid hydrolysis:

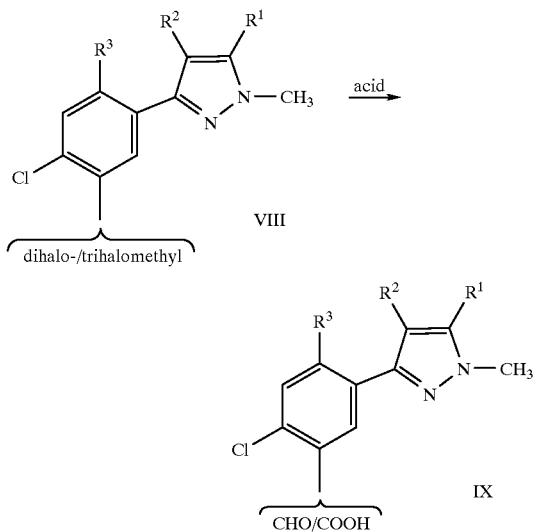

Particularly suitable substances are strong acids, such as sulfuric and hydrochloric acid, the reaction temperature usually being from 50 to 100° C.

The aldehydes IX' can then be converted into carboxylic acids IX" or ketones X in a manner known per se (cf., in this context, for example Houben-Weyl, Methoden der Organischen Chemie [Methods of Organic Chemistry], Georg Thieme Verlag Stuttgart, 4th Edition, Vol. 6/1a, 1980, p. 946 et seq., Vol. 7/2a, 1973, p. 699 et seq. and Vol. 8, 1952, p. 404 et seq.):

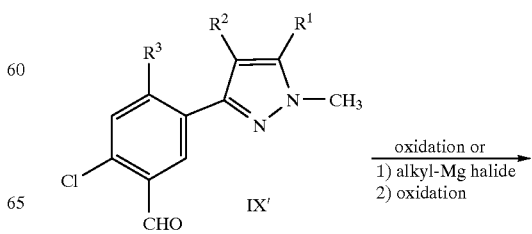

-continued

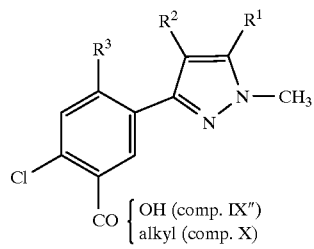

The aldehyde IX' can either be oxidized to give the corresponding carboxylic acid IX", or IX' is first reacted with an organometal compound, preferably a Grignard compound (an alkylmagnesium halide) to give a secondary alcohol which is subsequently oxidized.

Compounds I where $R^4$=CHF$_2$, CF$_3$ or CF$_2$—(C$_1$–C$_3$-alkyl) can then be obtained from IX and X in a manner known per se {see, for example, M. Scholz, H. W. Roesky, D. Stalke, K. Keller, F. T. Edelmann, J. Organomet. Chem. 366 (1989) 73} by means of reaction with a fluorinating agent, preferably sulfur tetrafluoride or diethylaminosulfur trifluoride (DAST):

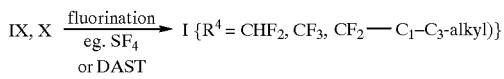

Furthermore, compounds I where $R^4$=cyano are also accessible from the aldehydes IX' in a manner known per se. To this end, IX is first reacted with hydroxylamine to give the oxime, whereupon the latter is dehydrated, for example by means of reaction with diphosgene (cf., for example, Houben-Weyl, Methoden der Organischen Chemie [Methods of Organic Chemistry], Georg Thieme Verlag Stuttgart, 4th Edition, Vol. 10/4, 1968, p. 55 et seq. and Vol. 8, 1952, p. 325 et seq.):

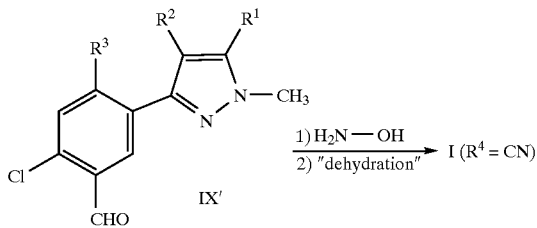

D) Acetalization of the aldehydes IX' or the ketones X in a manner known per se in the presence of an acid catalyst (cf., for example, Houben-Weyl, Methoden der Organischen Chemie [Methods of Organic Chemistry], Georg Thieme Verlag Stuttgart, Vol. 6/3, 4th Edition 1965, p. 204 et seq., p. 221 et seq.; ditto Vol. 9, 4th Edition 1955, p. 199 et seq. and Vol. E14a/3, 1992, p. 415 et seq.):

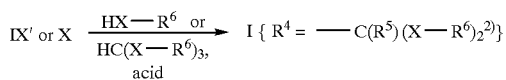

2) In this case, thus, Y=X and $R^6$=$R^7$.

Examples of suitable acid catalysts are toluenesulfonic acid, hydrochloric acid or sulfuric acid.

The process products can be subjected to a transacetalization in a manner known per se using other alcohols or thiols $R^7$-YH in the presence of catalytic amounts of acid or of a Lewis acid (eg. boron trifluoride) (see, in this context, for example, Houben-Weyl, Methoden der Organischen Chemie [Methods of Organic Chemistry], Georg Thieme Verlag, Stuttgart, Vol. E14a/1, 1991, p. 803 et seq. and Vol. E14a/3, 1992, p. 414 et seq.):

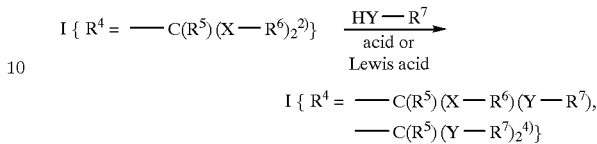

4) In this case, thus, X=Y and $R^6$=$R^7$.

E) C—C linkage between compounds VII where $R^{10}$= bromine or iodine and metal cyanides or fluorinated alkyl/alkenyl halides:

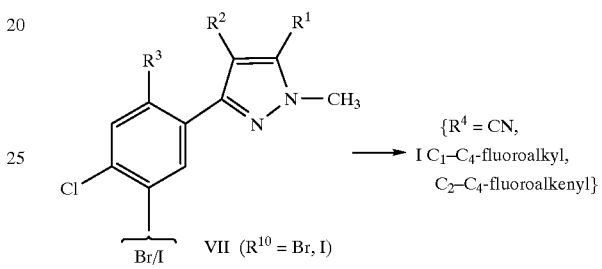

Compounds I where $R^4$=cyano can be prepared, as a rule, in a manner known per se (see, for example, Houben-Weyl, Methoden der Organischen Chemie [Methods of Organic Chemistry], Georg Thieme Verlag, Stuttgart, Vol. E5, 1985, p. 1459 et seq.) by reacting VII ($R^{10}$=Br, I) with an alkali metal cyanide or with copper cyanide.

The process is usually carried out in a polar organic solvent, eg. in dimethylformamide or an ether such as tetrahydrofuran.

The reaction is preferably carried out in the presence of a transition-metal catalyst, such as tetrakis(triphenylphosphine)palladium.

To prepare I where $R^4$=fluoroalkyl or fluoroalkenyl, VII ($R^{10}$=Br or I) is preferably reacted in a manner known per se with alkali metal perfluoroalkanecarboxylic acid salts and copper(I) iodide {cf. U.S. Pat. No. 4,814,480; K. Matsui, Chem. Lett., 1719 (1981); J. N. Freskos, Synth. Commun. 18 (1988) 965}, with fluoroalkenyl halides, palladium acetate and a base {cf. DE-A 40 13 305; W. Heitz, A. Knebelkamp, Makromol. Chem.-Rapid 12 (1991) 69} or with fluoroalkenyl copper or tin compounds in the presence of tetrakis(triphenylphosphine)palladium {cf. P. L. Heinze, D. J. Burton, J. Fluorine Chem. 31 (1986) 115; D. J. Burton, S. W. Hansen, J. Am. Chem. Soc. 108 (1986) 4229}.

Unless otherwise indicated, the reactions described above are expediently carried out under atmospheric pressure or under the inherent pressure of the reaction mixture in question.

As a rule, the mixtures are worked up by known methods, for example by diluting the reaction solution with water and subsequently isolating the product by means of filtration, crystallization or solvent extraction, or by removing the solvent, partitioning the residue in a mixture of water and a suitable organic solvent and working up the organic phase to give the product of value.

The substituted 1-methyl-3-phenylpyrazoles I can be obtained from their preparation in the form of isomer mixtures, but, if desired, the latter can be resolved into the essentially pure isomers by the methods customary for such cases, such as crystallization or chromatography, also on an optically active adsorbate. Pure optically active isomers can be prepared advantageously from suitable optically active starting materials.

Agriculturally useful salts of the compounds I can be formed in a manner known per se by means of reaction with an acid of the corresponding anion, preferably of hydrochloric acid, hydrobromic acid, sulfuric acid, phosphoric acid or nitric acid.

The compounds I and their agriculturally useful salts are suitable, in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soya and cotton without causing any essential damage to the crop plants. This effect is mainly observed at low rates of application.

Depending on the application method in question, the compounds I, or herbicidal compositions comprising them, can additionally be employed in a further number of crop plants for eliminating undesirable plants. Examples of suitable crops are the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

In addition, the compounds I may also be used in crops which are tolerant to the action of herbicides due to breeding, including genetic engineering methods.

Moreover, the substituted 1-methyl-3-phenylpyrazoles I are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

Also of economic interest is to facilitate harvesting, which is made possible by concentrating, over a period of time, dehiscence, or reducing the adherence to the tree, in citrus fruit, olives or other species and varieties of pomaceous fruit, stone fruit and nuts. The same mechanism, ie. promotion of the formation of abscission tissue between fruit or leaf and shoot of the plants, is also important for readily controllable defoliation of useful plants, in particular cotton.

Moreover, shortening the period within which the individual cotton plants mature results in improved fiber quality after harvesting.

The compounds I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should guarantee the finest possible distribution of the active ingredients according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active ingredient, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active ingredients together with a solid carrier.

Granules, eg coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the active ingredients I in the ready-to-use preparations can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

The formulation examples which follow illustrate the preparation of such products:

I. 20 parts by weight of the compound No. Ia.002 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the compound No. Ib.011 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. Ib.002 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. Ib.001 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of the active ingredient No. Ia.049 are mixed with 97 parts by weight of finely divided kaolin. This gives a dust which comprises 3% by weight of active ingredient.

VI. 20 parts by weight of the active ingredient No. Ib.052 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. Ib.051 is dissolved in a mixture composed of 70 parts by weight of cyclohexanone, 20 parts by weight of ethoxylated isooctylphenol and 10 parts by weight of ethoxylated castor oil. The mixture can then be diluted with water to the desired concentration of active ingredient. This gives a stable emulsion concentrate.

VIII. 1 part by weight of the compound No. Ib.049 is dissolved in a mixture composed of 80 parts by weight of cyclohexanone and 20 parts by weight of Wettol® EM 31 (=nonionic emulsifier based on ethoxylated castor oil). The mixture can then be diluted with water to the desired concentration of active ingredient. This gives a stable emulsion concentrate.

The active ingredients I or the herbicidal compositions can be applied pre- or post-emergence. If the active ingredients are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active ingredients reach the leaves of undesirable plants growing underneath, or the bare soil surface (post-directed, lay-by).

The rates of application of active ingredient I are from 0.001 to 3.0, preferably 0.01 to 1.0, kg/ha of active substance (a.s.), depending on the control target, the season, the target plants and the growth stage.

To widen the spectrum of action and to achieve synergistic effects, the substituted 1-methyl-3-phenylpyrazoles I may be mixed with a large number of representatives of other herbicidal or growth-regulating active ingredients and then applied concomitantly. Suitable components for mixtures are 1,2,4-thiadiazole, 1,3,4-thiadiazole, amides, aminophosphoric acid and its derivatives, aminotriazoles, anilides, aryloxy-/hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivates, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

Preparation Examples

EXAMPLE 1

4-Chloro-3-(4-chloro-2-fluoro-5-trifluoromethylphenyl)-5-difluoromethoxy-1-methyl-1H-pyrazole (No. Ib. 052)

1 g (2.8 mmol) of 2-chloro-5-(4-chloro-5-difluoromethoxy-1-methyl-1H-pyrazol-3-yl)-4-fluorobenzoic acid was introduced into a 500 ml autoclave made of Hastelloy C. This was subsequently made inert using nitrogen. The autoclave was placed into a cold bath of dry ice/acetone and charged first with 20 g (1 mol) of hydrogen fluoride and then with 5 g (0.046 mol) of sulfur tetrafluoride. The stirred mixture was subsequently allowed to come to room temperature, and the temperature was then increased to 105° C. Stirring was continued for 10 hours at this internal temperature, during which process a maximum pressure rise to 6.4 bar was observed. After the experiment has ended, the batch was cooled to 25° C., whereupon the mixture was degassed in a washing tower using potassium hydroxide solution. In the autoclave, the residue was then taken up in 50 ml of dichloromethane. The mixture was poured into 50 ml of ice-water. The organic phase was thereupon separated off, after 1 hour washed using 50 ml of water, dried over 4 g of a 1:1 mixture of potassium fluoride/ magnesium sulfate and finally concentrated under reduced pressure. The crude product obtained (0.8 g) was purified by chromatography on silica gel (eluent: cyclohexane/methyl tert-butyl ether, ratio 5:1). After the fractions comprising product of value had been combined, the solvent was removed. Yield: 0.45 g of the desired product of value in the form of an amorphous solid.

$^1$H NMR (250 MHz; in CDCl$_3$): δ [ppm]=3.85 (s,3H), 6.70 (t,1H), 7.35 (d,1H), 7.95 (d,1H).

Precursor 1.1

5-(4-Chloro-2-fluoro-5-methylphenyl)-1,2-dihydro-2-methyl-3H-pyrazol-3-one 34.7 g (0.75 mol) of methylhydrazine were added to a solution of 177 g (0.68 mol) of ethyl 3-(4-chloro-2-fluoro-5-methylphenyl)-3-oxopropionate in 500 ml of diethylene glycol. After 6 hours at 100° C., the mixture was poured into 4 l of water. The solids were subsequently separated off and dried. Yield: 133 g; m.p.: 155–156° C.

Precursor 1.2

3-(4-Chloro-2-fluoro-5-methylphenyl)-5-difluoromethoxy-1-methyl-1H-pyrazole

Gaseous chlorodifluoromethane was passed at room temperature for 2 hours into a solution of 133 g (0.55 mol) of 5-(4-chloro-2-fluoro-5-methylphenyl)-1,2-dihydro-2-methyl-3H-pyrazol-3-one and 110 g (2.7 mol) of sodium hydroxide in 1 l of dioxane and 0.5 l of water. The reaction solution was then poured into 2 l of water, whereupon the aqueous phase was extracted three times using ethyl acetate. The combined organic phases were dried over magnesium sulfate and then filtered and concentrated. The residue was purified by means of column chromatography on silica gel (eluent: cyclohexane/ethyl acetate=9:1), followed by preparative MPLC on silica gel (same eluent). Yield: 43 g.

$^1$H NMR (250 MHz; in CDCl$_3$): δ [ppm]=2.37 (s,3H), 3.80 (s,3H), 6.30 (s,1H), 6.57 (t,1H), 7.14 (d,1H), 7.82 (d,1H).

Precursor 1.3

4-Chloro-3-(4-chloro-2-fluoro-5-methylphenyl)-5-difluoromethoxy-1-methyl-1H-pyrazole 22 g (0.16 mol) of sulfuryl chloride were added dropwise to a solution of 43 g (0.15 mol) of 3-(4-chloro-2-fluoro-5-methylphenyl)-5-difluoromethoxy-1-methyl-1H-pyrazole in 250 ml of tetrachloromethane. After the reaction solution had subsequently been stirred for 16 hours, 200 ml of saturated aqueous sodium hydrogen carbonate solution were added dropwise. The organic phase was thereupon separated off, washed using saturated sodium chloride solution, dried over magnesium sulfate, then filtered and subsequently concentrated. Yield: 46 g.

$^1$H NMR (250 MHz; in CDCl$_3$): δ [ppm]=2.37 (s,3H), 3.84 (s,3H), 6.71 (t,1H), 7.21 (d,1H), 7.40 (d,1H).

Precursor 1.4

4-Chloro-3-(4-chloro-5-dibromomethyl-2-fluorophenyl)-5-difluoromethoxy-1-methyl-1H-pyrazole A solution of 46 g (0.14 mol) of 4-chloro-3-(4-chloro-2-fluoro-5-methylphenyl)-5-difluoromethoxy-1-methyl-1H-pyrazole and 62.9 g (0.35 mol) of N-bromosuccinimide in 2 l of tetrachloromethane was irradiated for 3.5 hours with a 1500 watt high-pressure mercury vapor lamp and a UV lamp. The solids were subsequently filtered off and washed twice more using tetrachloromethane. The combined filtrates were then concentrated. Yield: 68 g.

$^1$H NMR (270 MHz; in CDCl$_3$): δ [ppm]=3.86 (s,3H), 6.72 (t,1H), 7.05 (s,1H), 7.19 (d,1H), 8.23 (d,1H).

Precursor 1.5

2-Chloro-5-(4-chloro-5-difluoromethoxy-1-methyl-1H-pyrazol-3-yl)-4-fluorobenzaldehyde 68 g (0.14 mol) of 4-chloro-3-(4-chloro-5-dibromomethyl-2-fluorophenyl)-5-difluoromethoxy-1-methyl-1H-pyrazole were dissolved in 200 ml of concentrated sulfuric acid, with ice-cooling, whereupon the mixture was heated at 100° C. until the evolution of gas had ceased. It was then poured into 4 l of ice-water. The mixture was subsequently extracted three times using ethyl acetate. The combined organic phases were washed with water, then dried over magnesium sulfate and finally concentrated. The crude product was purified by means of column chromatography on silica gel (eluent: hexane/ethyl acetate=8:1). Yield: 35 g; m.p.: 95–98° C.

Precursor 1.6

2-Chloro-5-(4-chloro-5-difluoromethoxy-1-methyl-1H-pyrazol-3-yl)-4-fluorobenzoic acid A solution of 2.8 g (18 mmol) of sodium dihydrogen phosphate dihydrate in 28 ml of water was added at 10–15° C. to a solution of 24 g (71 mmol) of 2-chloro-5-(4-chloro-5-difluoromethoxy-1-methyl-1H-pyrazol-3-yl)-4-fluorobenzaldehyde in 130 ml of acetonitrile. Then, 6.8 ml of 30% strength aqueous hydrogen peroxide solution and (in the course of one hour) 9.8 g (108 mmol) of sodium chlorite were added in succession. After the mixture had been stirred for a further hour, it was heated to room temperature. After it had been stirred for a further 16 hours, it was acidified using dilute hydrochloric acid. The aqueous solution was then extracted twice using ethyl acetate, whereupon the combined organic phases were washed in succession with concentrated aqueous thiosulfate solution, water and saturated sodium chloride solution, dried over magnesium sulfate and finally concentrated. Yield: 23 g; m.p.: 137–140° C.

EXAMPLE 2

4-Chloro-3-(4-chloro-2-fluoro-5-di(methylthio) methylphenyl)-5-difluoromethoxy-1-methyl-1H-pyrazole (No. 1b.011)

1.1 g (15 mmol) of sodium thiomethoxide were added, with ice-cooling, to a solution of 1.5 g (3 mmol) of 4-chloro-3-(4-chloro-5-dibromomethyl-2-fluorophenyl)-5-difluoromethoxy-1-methyl-1H-pyrazole in 30 ml of dimethyl sulfoxide. After 16 hours at room temperature, the mixture was poured into 0.5 l of water. The aqueous phase was subsequently extracted twice using ethyl acetate, whereupon the combined organic phases were washed water and saturated aqueous sodium chloride solution, dried over magnesium sulfate and finally concentrated. The crude product was purified by means of silica gel chromatography (eluent: hexane/ethyl acetate=9:1).

Yield: 0.2 g.

$^1$H NMR (270 MHz; in CDCl$_3$): δ [ppm]=2.14 (s,6H), 3.84 (s,3H), 5.28 (s,1H), 6.70 (t,1H), 7.25 (d,1H), 7.86 (d,1H).

EXAMPLE 3

4-Chloro-3-(4-chloro-2-fluoro-5-di(ethoxy) methylphenyl)-5-difluoromethoxy-1-methyl-1H-pyrazole (No. 1b.002)

20 ml of triethyl orthoformate and 0.1 g of toluenesulfonic acid were added to a solution of 3 g (8.8 mmol) of 2-chloro-5-(4-chloro-5-difluoromethoxy-1-methyl-1H-pyrazol-3-yl)-4-fluorobenzaldehyde in 50 ml of tetrahydrofuran. After the mixture had been refluxed for 2 hours, it was treated with 3 ml of triethylamine. The mixture was subsequently concentrated. The residue was treated with 50 ml of water. The product was subsequently extracted from the aqueous phase using ethyl acetate. The organic phase was then washed using saturated aqueous sodium hydrogen carbonate solution, dried over magnesium sulfate and finally concentrated. The crude product was purified by means of column chromatography on silica gel (eluent: hexane/ethyl acetate= 9:1). Yield: 1 g.

$^1$H NMR (270 MHz; in CDCl$_3$): δ [ppm]=1.25 (t,6H), 3.64 (m,4H), 3.84 (s,3H), 5.71 (s,1H), 6.70 (t,1H), 7.22 (d,1H), 7.87 (d,1H).

EXAMPLE 4

4-Chloro-3-(4-chloro-5-difluoromethyl-2-fluorophenyl)-5-difluoromethoxy-1-methyl-1H-pyrazol (No. 1b.051)

0.9 g (5.4 mmol) of diethylaminosulfur tetrafluoride (DAST) were added dropwise at 50° C. to 0.9 g (2.7 mmol) of 2-chloro-5-(4-chloro-5-difluoromethoxy-1-methyl-1H-pyrazol-3-yl)-4-fluorobenzaldehyde. The reaction mixture was subsequently stirred at this temperature for a further 1.5 hours. The batch was then poured onto 10 g of ice, whereupon 10 ml of dichloromethane were added. The organic phase was separated off and washed twice using water (10 ml), then dried and concentrated under reduced pressure. The resulting crude product was purified by chromatography on 30 g of silica gel (eluent: cyclohexane/methyl tert-butyl ether in a ratio of 4:1). Yield after removal of the solvent: 0.35 g of product of value in the form of a viscous oil.

$^1$H NMR (400 MHz; in CDCl$_3$): δ [ppm]=3.83 (s,3H), 6.72 (t,1H), 6.94 (t,1H), 7.28 (d,1H), 7.90 (d,1H).

EXAMPLE 5

2-Chloro-5-(4-chloro-5-difluoromethoxy-1-methyl-1H-pyrazol-3-yl)-4-fluorobenzonitrile (No. 1b.049)

1.2 g (18 mmol) of hydroxylamine hydrochloride and 1.8 g (23 mmol) of pyridine were added to 2 g (5.9 mmol) of 2-chloro-5-(4-chloro-5-difluoromethoxy-1-methyl-1H-pyrazol-3-yl)-4-fluorobenzaldehyde, whereupon the mixture is dissolved in 100 ml of methanol. The mixture was subsequently stirred first for 16 hours at approximately 20° C. and then for another 2 hours at reflux temperature. The mixture was then concentrated. The residue was treated with water. The reaction product was extracted from the aqueous phase using ethyl acetate. The organic phase was finally dried over magnesium sulfate and concentrated.

The resulting oxime was then first dissolved in 50 ml of acetonitrile, and 1.3 g (6.7 mmol) of diphosgene were then added to the solution. After the reaction mixture had been stirred for 30 minutes, it was treated with 100 ml of water and stirred for a further 16 hours. The product of value was then extracted using diethyl ether. The ether phase was washed with water, dried over magnesium sulfate and concentrated. The residue was purified by means of column chromatography on silica gel (eluent: hexane/ethyl acetate= 7:1).

Yield: 0.6 g; m.p.: 93–95° C.

Other 1-methyl-3-phenylpyrazoles I which were, or can be, prepared in a similar manner are listed in Table 2 below, in addition to the compounds described above:

TABLE 2

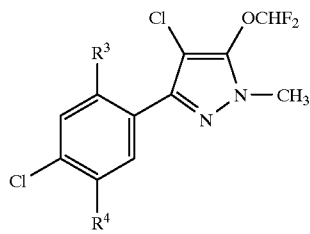

($R^1$ = OCHF$_2$; $R^2$ = Cl)

| No. | $R^3$ | $R^4$ | M.p./$^1$H NMR [ppm]/MS [m/z] |
|---|---|---|---|
| Ia.002 | Cl | —CH(OC$_2$H$_5$)$_2$ | 28 [M]$^+$ |
| Ia.049 | Cl | —CN | 84–86° C. |
| Ib.001 | F | —CH(OCH$_3$)$_2$ | 68–69° C. |
| Ib.002 | F | —CH(OC$_2$H$_5$)$_2$ | 1.25(t, 6H), 3.64(m, 4H), 3.84 (s, 3H), 5.71(s, 1H), 6.70 (t, 1H), 7.22(d, 1H), 7.87(d, 1H) |
| Ib.011 | F | —CH(SCH$_3$)$_2$ | 2.14(s, 6H), 3.84(s, 3H), 5.28 (s, 1H), 6.70(t, 1H), 7.25 (d, 1H), 7.86(d, 1H) |
| Ib.049 | F | —CN | 3.85(s, 3H), 6.71(t, 1H), 7.39(d, 1H), 7.93(d, 1H) |
| Ib.051 | F | —CHF$_2$ | 3.83(s, 3H), 6.72(t, 1H), 6.94 (t, 1H), 7.28(d, 1H), 7.90(d, 1H) |
| Ib.052 | F | —CF$_3$ | 3.85(s, 3H), 6.70(t, 1H), 7.35(d, 1H), 7.95(d, 1H) |

Use examples (herbicidal activity)

The herbicidal activity of the substituted s-methyl-3-phenylpyrazoles I was demonstrated by the following greenhouse experiments: the culture containers used were plastic flowerpots containing loamy soil with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with translucent plastic hoods until the plants had rooted. This cover causes uniform germination of the test plants, unless this was adversely affected by the active ingredients.

For the post-emergence treatment, the test plants were first grown to a plant height of 3 to 15 cm, depending on the plant habit, and only then treated with the active ingredients which had been suspended or emulsified in water. The test plants for this purpose were either sown directly and grown in the same containers, or they were first grown separately as seedlings and transplanted into the test containers a few days prior to the treatment. The rate of application for the post-emergence treatment was 0.5 kg/ha of a.s. (active substance).

Depending on the species, the plants were kept at from 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific name | Common name |
| --- | --- |
| Echinochloa crus-galli | barnyard grass |
| Galium aparine | catchweed bedstraw |
| Ipomoea subspecies | morningglory |
| Viola arvensis | field pansy; field violet |

The compound No. Ib.052, applied post-emergence, showed a very good activity against the abovementioned weeds at a rate of application of 0.5 kg/ha of a.s.

Use Examples (desiccant/defoliant activity)

The test plants used were young cotton plants with 4 leaves (without cotyledons) which had been grown under greenhouse conditions (relative atmospheric humidity 50 to 70%; day/night temperature 27/20° C.).

The young cotton plants were subjected to foliar treatment to runoff point with aqueous preparations of the active ingredients (with an addition of 0.15% by weight of the fatty alcohol alkoxide Plurafac® LF 700[6]), based on the spray mixture). The amount of water applied was 1000 l/ha (converted). After 13 days, the number of leaves shed and the degree of defoliation in % were determined.

[6]a low-foaming moniaonic surfactant by BASF AG

No leaves were shed in the untreated control plants.

We claim:

1. A substituted 1-methyl-3-phenylpyrazole of the formula I

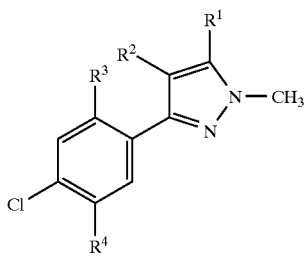

where the substituents have the following meanings:
$R^1$ is $C_1$–$C_4$-haloalkoxy or $C_1$–$C_4$-haloalkylthio;
$R^2$ is halogen;
$R^3$ is fluorine or chlorine;
$R^4$ is cyano, $C_1$–$C_4$-fluoroalkyl, $C_2$–$C_4$-fluoroalkenyl or —$C(R^5)(X-R^6)(Y-R^7)$, where
$R^5$ is hydrogen or $C_1$–$C_4$-alkyl, X and Y independently of one another are oxygen or sulfur and
$R^6$ and $R^7$ independently of one another are $C_1$–$C_4$-alkyl, $C_1$–$C_4$-haloalkyl, $C_3$–$C_4$-alkenyl, $C_3$–$C_4$-haloalkenyl or $C_3$–$C_4$-alkynyl;
and to the agriculturally useful acid addition salts of I.

2. A substituted 1-methyl-3-phenylpyrazole of the formula I or an acid addition salt thereof, as claimed in claim 1, where $R^4$ is cyano.

3. A substituted 1-methyl-3-phenylpyrazole of the formula I or an acid addition salt thereof, as claimed in claim 1, where $R^4$ is $C_1$–$C_4$-fluoroalkyl or $C_2$–$C_4$-fluoroalkenyl.

4. A substituted 1-methyl-3-phenylpyrazole of the formula I or an acid addition salt thereof, as claimed in claim 1, where $R^4$ is —$C(R^5)(X-R^6)(Y-R^7)$.

5. A herbicidal composition comprising a herbicidally active amount of at least one substituted 1-methyl-3-phenylpyrazole of the formula I or of an acid addition salt of I, as claimed in claim 1, and at least one liquid and/or solid carrier and, if desired, at least one surfactant.

6. A composition for the desiccation and/or defoliation of plants, comprising such an amount of at least one substituted 1-methyl-3-phenylpyrazole of the formula I or of an acid addition salt of I, as claimed in claim 1, that it acts as a desiccant and/or defoliant, and at least one inert liquid and/or solid carrier and, if desired, at least one surfactant.

7. A process for the preparation of herbicidally active compositions, which comprises mixing a herbicidally active amount of at least one substituted 1-methyl-3-phenylpyrazole of the formula I or of an acid addition salt of I, as claimed in claim 1, with at least one liquid and/or solid carrier and, if desired, at least one surfactant.

8. A process for the preparation of compositions which act as desiccants and/or defoliants, which comprises mixing such an amount of at least one substituted 1-methyl-3-phenylpyrazole of the formula I or of an acid addition salt of I, as claimed in claim 1, that it acts as a desiccant and/or defoliant, with at least one liquid and/or solid carrier and, if desired, at least one surfactant.

9. A method for controlling undesirable vegetation, which comprises allowing a herbicidally active amount of at least one substituted 1-methyl-3-phenylpyrazole of the formula I or of an acid addition salt of I, as claimed in claim 1, to act on plants, their environment or on seed.

10. A method for the desiccation and/or defoliation of plants, which comprises allowing such an amount of at least one substituted 1-methyl-3-phenylpyrazole of the formula I or of an acid addition salt of I, as claimed in claim 1, to act on plants that it has a desiccant/defoliant action.

11. A method as claimed in claim 10, wherein cotton is treated.

* * * * *